United States Patent
Shirataki et al.

(10) Patent No.: US 8,653,246 B2
(45) Date of Patent: *Feb. 18, 2014

(54) METHOD FOR PURIFYING PROTEIN

(75) Inventors: Hironobu Shirataki, Tokyo (JP); Naoyuki Shinohara, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 471 days.

This patent is subject to a terminal disclaimer.

(21) Appl. No.: 12/681,189

(22) PCT Filed: Sep. 26, 2008

(86) PCT No.: PCT/JP2008/067540
§ 371 (c)(1),
(2), (4) Date: Apr. 1, 2010

(87) PCT Pub. No.: WO2009/054226
PCT Pub. Date: Apr. 30, 2009

(65) Prior Publication Data
US 2010/0228010 A1   Sep. 9, 2010

(30) Foreign Application Priority Data
Oct. 26, 2007   (JP) .................. 2007-279406

(51) Int. Cl.
*A23J 1/00* (2006.01)
*C07K 1/00* (2006.01)
*B01J 20/26* (2006.01)

(52) U.S. Cl.
USPC .................. 530/416; 530/412; 502/402

(58) Field of Classification Search
None
See application file for complete search history.

(56) References Cited

U.S. PATENT DOCUMENTS

| | | |
|---|---|---|
| 5,064,866 A | 11/1991 | Toyomoto et al. |
| 5,547,575 A | 8/1996 | Demmer et al. |
| 5,739,316 A | 4/1998 | Beer et al. |
| 6,001,974 A | 12/1999 | Demmer et al. |
| 6,177,548 B1 | 1/2001 | Wan et al. |
| 6,235,892 B1 | 5/2001 | Demmer et al. |
| 6,780,327 B1 | 8/2004 | Wu et al. |
| 6,783,937 B1 | 8/2004 | Hou et al. |
| 2002/0010319 A1 | 1/2002 | Ansaldi et al. |
| 2005/0107594 A1 | 5/2005 | Sun et al. |
| 2005/0272917 A1 | 12/2005 | Jiao et al. |
| 2007/0112178 A1 | 5/2007 | Johansson et al. |
| 2007/0167613 A1 | 7/2007 | Johansson et al. |
| 2007/0259453 A1 | 11/2007 | Engstrand et al. |
| 2009/0050566 A1 | 2/2009 | Kozlov et al. |

FOREIGN PATENT DOCUMENTS

| | | |
|---|---|---|
| JP | 2-132132 | 5/1990 |
| JP | 2796995 | 7/1998 |
| JP | 11-012300 | 1/1999 |
| JP | 2002-517406 | 6/2002 |
| JP | 2007-532477 | 11/2007 |
| JP | 2008-500972 | 1/2008 |
| JP | 2008-505851 | 2/2008 |
| JP | 2008-517906 | 5/2008 |
| JP | 2009-53191 | 3/2009 |
| JP | 2010-70490 | 4/2010 |
| JP | 2010-158624 | 7/2010 |
| JP | 2010-241761 A | 10/2010 |
| WO | 95/32793 | 12/1995 |
| WO | 00/50160 | 8/2000 |
| WO | 01/40448 | 6/2001 |
| WO | 02/085519 | 10/2002 |
| WO | 2009/054226 | 4/2009 |

OTHER PUBLICATIONS

Okamura et al. "Solvent effect on protein binding by polymer brush grafted onto porous membranes" J. Chromatography A, 953, 2002, 101-109.*
International Preliminary Report on Patentability, including the Written Opinion (in English) for PCT/JP2008/067540, mailed Jun. 10, 2010.
U.S. Appl. No. 13/381,129, filed Jan. 20, 2012.
Platonova, G.A. et al., "Quantitative fast fractionation of a pool of polyclonal antibodies by immunoaffinity membrane chromatography.", J. Chromatgr. A. vol. 852, 1999, pp. 129-140.
Takanobu Sugo et al., "Hoshasen Graft Jugo ni Okeru ko Kinoka Saizensen Saishukai Hoshasen Graft Jugo Gijutsu o ojo shita Shin Sozai no Sosei", Convertech, vol. 33, No. 12, 2005, pp. 34-38.
Search report from PCT/JP2010/061031, mail date is Aug. 3, 2010.
International Preliminary Report on Patentability, including the Written Opinion (in English) for PCT/JP2010/061031, mailed Feb. 14, 2012.
Henry R. Charlton et al., "Characterisation of a generic monoclonal antibody harvesting system for adsorption of DNA by depth filters and various membranes," Bioseparation, vol. 8, pp. 281-291, 1999.
International Search Report for PCT/JP2008/067540, mailed Dec. 22, 2008.
International Preliminary Report on Patentability for PCT/JP2008/067540, issued Jun. 1, 2010.

(Continued)

Primary Examiner — Daniel E Kolker
Assistant Examiner — James Rogers
(74) Attorney, Agent, or Firm — Greenblum & Bernstein, P.L.C.

(57) ABSTRACT

The present invention provides a method for purifying a protein to remove impurities from a mixture liquid containing a desired protein and the impurities, comprising the step of performing filtration using a porous membrane having a graft chain on a pore surface and an anion-exchange group fixed to the graft chain.

19 Claims, 5 Drawing Sheets

(56) References Cited

OTHER PUBLICATIONS

English Translation of International Preliminary Report on Patentability and Written Opinion for International Application No. PCT/JP2010/061031, mailed Feb. 23, 2012.

Saito K et al., "Radiation-induced graft polymerization is the key to develop high-performance functional materials for protein purification", Radiation Physics and Chemistry, Elsevier Science Publishers BV., Amsterdam, NL, vol. 54, No. 5, XP004161328, May 1, 1999, pp. 517-525.

Yonedu Shinji et al., "Affinity elution of gelsolin adsorbed onto an anion-exchange porous membrane", Membrane, vol. 30, No. 5, 2005, XP008142475, , pp. 269-274.

Hagiwara K et al., "High-performance purification of gelsolin from plasma using anion-exchange porous hollow-fiber mambrane", Journal of Chromatography B: Biomedical Sciences & Applications, Elsevier, Amsterdam, NL, vol. 821, No. 2, XP004974125, Jul. 25, 2005, pp. 153-158.

Kubota N et al., "Module performance of anion-exchange porous hollow-fiber membranes for high-speed protein recovery", Journal of Chromatography, Elsevier Science Publishers B.V.NL, XP004096270, Oct. 10, 1997, pp. 159-165.

Tsuneda S et al., "High-throughput processing of proteins using a porous and tentacle anion-exchange membrane", Journal of Chromatography, Elsevier Science Publishers B.V.NL, vol. 689, No. 2, XP004023269, Jan. 13, 1995, pp. 211-218.

Ito H, "Comparison of 1-typhtophan binding capacity of BSA captured by a polymer brush with that of BSA absorbed onto a gel network", Journal of Chromatography, Elsevier Science Publishers B.V.NL, XP004296297, Aug. 3, 2001, pp. 41-47.

Koguma et al. "Multilayer Binding of Proteins to Polymer Chains Grafted onto Porous Hollow-Fiber Membranes Containing Different Anion-Exchange Group," Biotechnology Progress, 2000, 16: 456-461.

Search report from E.P.O. that issued with respect to patent family member European Patent Application No. 08842007.0, mail date is Sep. 12, 2011.

"New Biochemical Experiments Course 1, Protein 1—separation, purification, properties-", Edited by the Japanese Biochemical Society, First edition, First printing, 1990, with English Translation thereof.

Japanese Office Action issued with respect to Japanese Application No. 2011-520924, mail date is Oct. 16, 2013.

\* cited by examiner

METHOD FOR PURIFYING PROTEIN

The present application is a U.S. national phase application of PCT/JP2008/067540, filed Sep. 26, 2008, which claims priority to JP 2007-279406, filed Oct. 26, 2007.

TECHNICAL FIELD

The present invention relates to a method for purifying a protein. Specifically, the present invention relates to a method for easily removing impurities from a mixture liquid containing a desired protein and the impurities, represented by an animal cell culture and efficiently purifying the desired protein.

BACKGROUND ART

In recent years, the practical large-scale purification of a protein has represented an important challenge in the biotechnology-based industry. Particularly in the field of medicine, demand for antibody drugs is rapidly increasing; there is a strong desire to establish technologies capable of efficiently producing and purifying large amounts of a protein.

A protein is generally produced by cell culture using a cell line derived from an animal. For practical use of a desired protein (hereinafter sometimes referred to simply as "a target protein"), particularly an antibody drug used as a medicine, it is necessary to remove cell debris and the like providing turbid components and a cell-derived dissolved protein and the like providing non-turbid components from a cell culture, followed by purification to such a degree as to give a composition sufficient for therapeutic application in humans.

A typical operation of purifying a target protein from a cell culture comprises first subjecting the cell culture to centrifugation to precipitate and remove turbid components; then, removing cell debris having a size of about 1 μm or less incapable of being completely removed by the centrifugation among the turbid components by means of size filtering using a microfiltration membrane; and further subjecting the filtrate to sterilization filtration using a filtration membrane having a maximum pore size of 0.22 μm or less for sterilization to provide a clear solution of the target protein (a harvest step). When the clear solution containing the target protein is obtained, the target protein is subsequently separated and purified using a purification process employing a combination of a plurality of chromatographic techniques including affinity chromatography (a downstream step). Impurity proteins produced from cells in the culture and dissolved in the culture are removed in the downstream step. In such a conventional method by which the target protein and the like are purified from the cell culture, the concentration of the target protein in the culture is typically 1 g/L or less, and the concentration of cell debris, dissolved impurity proteins and the like contained in the culture is also comparable to the concentration of the target protein. In the concentration range, the purification process using the conventional harvest and downstream steps is sufficiently useful in purifying the target protein.

However, a rapid increase in demand for antibody drugs allows the production of proteins providing the antibody drugs to be large-scale-oriented; fast-paced advances in culture techniques have recently increased the concentration of a target protein in a cell culture, which is about to reach as high as 10 g/L. Such fast-paced advances in culture techniques simultaneously mean the result as which impurity proteins also increase, causing the prediction of substantial loads applied to purification using a conventional protein purification process.

Hence, as a technique for purifying large amounts of a protein, for example, Patent Documents 1 and 2 each disclose a protein adsorption membrane to which protein adsorption capability is imparted by introducing ion-exchange groups into a porous membrane, which can also be purchased.

As a usage example of a protein adsorption membrane, Patent Document 3 also discloses a method for separating albumin from a lymph fluid using two types of protein adsorption membranes, i.e. a porous cellulose membrane into which anion-exchange groups are introduced and a porous cellulose membrane into which cation-exchange groups are introduced.

Further, Patent Document 4 discloses a method for separating nucleic acid and endotoxin using a porous cellulose membrane into which anion-exchange groups are introduced.

Still further, Patent Documents 5 and 6 disclose protein adsorption membranes in which cation-exchange groups and anion-exchange groups, respectively are introduced into porous polyether sulfone membranes.

Non-Patent Document 1 discloses a method for separating nucleic acid and monoclonal antibody using a porous membrane containing ion-exchange groups.

Patent Document 1: U.S. Pat. No. 5,547,575
Patent Document 2: U.S. Pat. No. 5,739,316
Patent Document 3: U.S. Pat. No. 6,001,947
Patent Document 4: U.S. Pat. No. 6,235,892
Patent Document 5: U.S. Pat. No. 6,783,937
Patent Document 6: U.S. Pat. No. 6,780,327
Non-Patent Document 1: Bioseparation 8:281-291, 1999

DISCLOSURE OF THE INVENTION

Problems to be Solved by the Invention

However, aggregated impurities are often observed to be contained in a recovered solution when a cell culture containing a high concentration of a target protein is subjected to centrifugation, microfiltration and sterilization filtration to make a clear fluid, which is then applied to a protein A affinity column as an affinity chromatography column to selectively adsorb the target protein, followed by eluting and recover the protein with an acidic eluent. With increasing number of repeated uses of the protein A affinity column, the amount of the aggregated impurities tends to be increased while the amount of the recovered target protein being decreased.

A larger amount of impurity proteins increases loads in the affinity chromatography step as described above, and not only requires a longer time of the purification step owing to the washing of the column and the like, but also results in shorter life of column beads used in the affinity chromatography, particularly the life of the protein A affinity column. It is undesirable for the protein A affinity column to have shorter life because the column is expensive.

In each of the methods disclosed in Patent Documents 1 to 4, the separation operation is performed after passing a stock solution used in the separation through a microfiltration membrane in advance to remove particulate impurities. This is because the protein adsorption membrane cannot remove particulate impurities since the protein adsorption membrane has a maximum pore size of as large as 3 μm to 5 μm.

Also in each of the methods disclosed in Patent Documents 5 and 6, the protein adsorption membrane cannot remove fine particulate impurities since it has a maximum pore size of 0.8 μm to 1.0 μm.

In addition, a cell culture generally contains a salt; when an ion-exchange membrane is used as disclosed in Non-Patent Document 1, impurity proteins cannot be practically removed from the cell culture because the amount of adsorption of proteins from a solution containing 0.1 M or more of the salt is markedly decreased.

As described above, the existing protein adsorption membranes have maximum pore sizes of about 0.8 μm or more and decreased amounts of adsorption in the presence of a salt. Thus it is not assumed that the adsorption membranes are used to simultaneously perform clarification intended to remove fine insoluble matter such as cell debris and adsorption of dissolved impurity proteins; the adsorption membranes are not suitable for the purpose.

Each of the protein adsorption membranes has a dynamic adsorption volume of 30 mg/mL or less per membrane volume even under conditions in which no salt is present in the solution; thus, a large amount of the protein adsorption membrane will be required to effectively adsorb and remove impurity proteins from the cell culture. In addition, each of these existing protein adsorption membranes is in the form of a flat membrane and therefore a large amount of the protein adsorption membrane cannot be housed in a compact size. As such, a large amount of the protein adsorption membrane housed in a large-size container will be required and thus cannot be said to be practical. The existing protein adsorption membranes having anion-exchange groups are more unsuitable for practical use because their amount of adsorption is markedly decreased when a salt is present in the solution.

In view of such circumstances, an object of the present invention is to provide a method for easily removing impurities from a mixture liquid containing a target protein and the impurities, represented by an animal cell culture and efficiently purifying the target protein.

Means for Solving the Problems

As the result of intensive studies for solving the above-described problems, the present inventors have found that the use of a porous membrane having graft chains on the pore surface and anion-exchange groups fixed to the graft chains is surprisingly effective to solve the above problems.

Thus, the present invention provides a method for purifying a protein and a porous hollow fiber membrane as described below.

[1] A method for purifying a protein to remove impurities from a mixture liquid containing a desired protein and the impurities, comprising the step of:
performing filtration using a porous membrane having a graft chain on a pore surface and an anion-exchange group fixed to the graft chain.

[2] The method for purifying the protein according to item [1] above, wherein the desired protein is one selected from the group consisting of monoclonal antibodies, polyclonal antibodies, humanized antibodies, human antibodies and immunoglobulins.

[3] The method for purifying the protein according to item [1] or [2] above, wherein the impurities are at least one selected from the group consisting of a non-turbid component and a turbid component dispersed in the mixture liquid.

[4] The method for purifying the protein according to item [3] above, wherein the non-turbid component is at least one selected from the group consisting of impurity proteins, HCP, DNA, viruses, endotoxins, proteaes and bacteria dissolved in the mixture liquid.

[5] The method for purifying the protein according to item [3] or [4] above, wherein the turbid component dispersed in the mixture liquid is at least one selected from the group consisting of cells and cell debris.

[6] The method for purifying the protein according to any one of items [1] to [5] above, wherein a salt concentration of the mixture liquid is from 0.01 M to 0.5 M (both inclusive).

[7] The method for purifying the protein according to any one of items [1] to [5] above, wherein a salt concentration of the mixture liquid is from 0.1 M to 0.3 M (both inclusive).

[8] The method for purifying the protein according to any one of items [1] to [7] above, wherein:
a base material of the porous membrane is polyethylene or polyvinylidene fluoride,
the graft chain is a polymer of glycidyl methacrylate and has a graft rate of from 10% to 250% (both inclusive), and
the graft chain has 70% or more of epoxy groups replaced with the anion-exchange groups.

[9] The method for purifying the protein according to item [8] above, wherein the graft rate is from 10% to 150% (both inclusive).

[10] The method for purifying the protein according to item [8] above, wherein the graft rate is from 10% to 90% (both inclusive).

[11] The method for purifying the protein according to item [8] above, wherein the graft rate is from 30% to 60% (both inclusive).

[12] The method for purifying the protein according to any one of items [1] to [11] above, wherein the anion-exchange group is a diethylamino group and/or a trimethylamino group.

[13] The method for purifying the protein according to any one of items [1] to [12] above, wherein the anion-exchange group is a diethylamino group.

[14] The method for purifying the protein according to any one of items [1] to [13] above, wherein the porous membrane has a maximum pore size of from 0.1 μm to 0.8 μm (both inclusive).

[15] The method for purifying the protein according to any one of items [1] to [14], wherein the mixture liquid is filtered using the porous membrane to remove one or more impurities comprising a non-turbid component.

[16] The method for purifying the protein according to any one of items [1] to [15], wherein the mixture liquid is an animal cell culture.

[17] The method for purifying the protein according to any one of items [1] to [16], wherein the porous membrane is a porous hollow fiber membrane.

[18] A porous hollow fiber membrane used in the method for purifying the protein according to item [17] above.

[19] A module comprising the porous hollow fiber membrane according to item [18] above.

[20] A porous hollow fiber membrane having a graft chain on a pore surface and an anion-exchange group fixed to the graft chain, wherein:
a base material of the porous hollow fiber membrane is polyethylene or polyvinylidene fluoride,
the graft chain is polymers of glycidyl methacrylate and has a graft rate of from 10% to 250% (both inclusive), and
the graft chain has 70% or more of epoxy groups replaced with the anion-exchange group.

[21] The porous hollow fiber membrane according to item [20] above, wherein the graft rate is from 10% to 150% (both inclusive).

[22] The porous hollow fiber membrane according to item [20] above, wherein the graft rate is from 10% to 90% (both inclusive).

[23] The porous hollow fiber membrane according to item [20] above, wherein the graft rate is from 30% to 60% (both inclusive).
[24] The porous hollow fiber membrane according to any one of items [20] to [23] above, wherein the porous membrane has a maximum pore size of from 0.1 μm to 0.8 μm (both inclusive).
[25] A module comprising the porous hollow fiber membrane according to any one of items [20] to [24] above.
[26] The method for purifying a protein according to any one of items [1] to [17] above, further comprising the step of performing purification using affinity chromatography.

ADVANTAGES OF THE INVENTION

In accordance with the method for purifying a protein according to the present invention, the clarification of a cell culture before an affinity chromatography step, carried out by the three steps of centrifugation, microfiltration and sterilization filtration can be easily performed through filtration using a porous membrane having graft chains and anion-exchange groups fixed to the graft chains.

In addition, removal of dissolved impurity proteins incapable of being removed by conventional methods can be made possible by filtration with the porous membrane having the fixed anion-exchange groups. Further, it is made possible to greatly reduce loads in the affinity chromatography step.

DESCRIPTION OF SYMBOLS

1 Cell culture tank
2 Perister pump
3 Pressure indicator (at entry side of module)
4 Anion-exchange hollow fiber membrane module
5 Pressure indicator (at exit side of module)
6 Flow control cock
7 Microfiltration hollow fiber membrane module for clarification

BEST MODE FOR CARRYING OUT THE INVENTION

A best mode for carrying out the present invention (hereinafter referred to as "the present embodiment") is described below in detail. Note that the present invention is not intended to be limited to the following embodiment, and various modifications can be made within the scope of the gist of the invention.

The method for purifying a protein according to the present embodiment is a method for purifying a protein to remove impurities from a mixture liquid represented by an animal cell culture, containing a desired protein useful as a medicine and the impurities, comprising the step of performing filtration using a porous membrane having a graft chain on a pore surface and an anion-exchange group fixed to the graft chain.

The method for purifying a protein according to the present embodiment is a method for purifying a protein which can easily remove impurities contained in a mixture liquid to provide a clear solution of a target protein.

Preferably, the method for purifying the protein according to the present embodiment further comprises the step of purifying the clear target protein solution obtained by the filtration step using affinity chromatography.

Examples of the mixture liquid containing a desired protein and impurities can include, but not limited to, an animal cell culture.

The animal cell culture is not particularly limited provided that it is a culture containing a target protein; however, examples thereof can include a culture containing a recombinant protein obtained by cell culture from host cells including Chinese hamster ovary (CHO) cells.

Examples of the target protein can include antibodies used as medicine; examples thereof can include monoclonal antibodies, polyclonal antibodies, humanized antibodies, human antibodies and immunoglobulins.

Examples of the impurities can include a turbid component dispersed in a mixture liquid and a non-turbid component.

Examples of the turbid and non-turbid components can include impurities other than a target protein contained in the culture obtained by performing animal cell culture in order to produce the desired protein.

Examples of the turbid component dispersed in a mixture liquid can include cells and cell debris; examples of the non-turbid component can include impurity proteins, host cell proteins (HCP), nucleic acids (DNA), viruses, endotoxins, proteases, and bacteria dissolved in the mixture liquid.

The method for purifying the protein according to the present embodiment preferably involves filtering the mixture liquid using the porous membrane to remove one or more impurities including the non-turbid component.

The non-turbid component can be removed by adsorption to the porous membrane. Preferably, the turbid component is also removed in removing one or more impurities including the non-turbid component.

The isopotential point (pI) of an antibody as a target protein ranges from about 6 to 8. A typical CHO animal cell culture has a pH ranging from roughly 7 to 8 and contains about 1% by mass (about 0.17 M) of a salt. The pH and salt concentration can vary depending on the type of the animal cell culture.

In an aqueous solution, the amino and carboxyl groups of the protein are present in ionized states: $-NH_3^+$ and $-COO^-$, respectively and the total charge of the protein in the aqueous solution depends on the pH of the culture. The total charge of the protein is zero at the pH of the isoelectric point (pI). The protein is made in a negatively charged state at a pH of more than pI, and in a positively charged state at a pH of less than pI.

Because an animal cell culture has a pH of from 7 to 8, a target protein is present in the culture in such a state that the protein has a total charge of nearly zero or is slightly positively charged; thus, the target protein is not substantially adsorbed by an anion-exchange group.

In contrast, the impurity proteins, host cell proteins (HCP), nucleic acids (DNA), endotoxins and the like dissolved in a mixture liquid are present in a negatively charged state in an animal cell culture even when dissolved in the culture because most of them have a pH of 6 or lower. The impurity proteins and the like dissolved in the mixture liquid have the property of being adsorbed by an anion-exchange group under conditions in which a salt is absent.

However, an animal cell culture typically contains a salt on the order of about 1% by mass (0.17 M) in practice, allowing few impurity proteins and the like to be adsorbed by an anion-exchange group even at a pI of 6 or lower. Thus, impurities cannot be directly removed from an animal cell culture even by use of a conventional adsorption membrane having anion-exchange groups or anion-exchange chromatography.

The method for purifying the protein according to the present embodiment can be used to purify even an animal cell culture having a salt concentration of from 0.01 M to 0.5 M (both inclusive).

According to the present embodiment, the salt concentration of the animal cell solution capable of being preferably purified is from 0.1 M to 0.3 M (both inclusive).

According to the present embodiment, when an animal cell culture is filtered using the porous membrane having the graft chains on the pore surface and the anion-exchange groups fixed to the graft chains, it has surprisingly been found that the impurity proteins, host cell proteins (HCP), nucleic acids (DNA), endotoxins and the like dissolved in the mixture liquid are adsorbed by the anion-exchange groups of the porous membrane despite that a salt is contained in the cell culture.

The porous membrane having graft chains on the pore surface and anion-exchange groups fixed to the graft chains is used in the filtration process to enable that adsorption of the impurity proteins, host cell proteins, nucleic acids, endotoxins and the like dissolved in a mixture liquid from an animal cell culture, which is not typically achieved. Although the detailed reason is unclear, the following is speculated.

In a common anion-exchange membrane and anion-exchange chromatography, anion-exchange groups are generally fixed to the surface of porous membrane pores or a resin and its pores. A protein is adsorbed by surface anion-exchange groups. The anion-exchange groups are fixed only to the surface of porous membrane pores or a resin and its pores and thereby rest two-dimensionally. As such, the protein is adsorbed in a point-contact manner on the surface of porous membrane pores or a resin and its pores; thus, the anion-exchange groups capable of being responsible for the adsorption are small in number. Thus, the presence of a salt in the solution significantly reduces the adsorption of the proteins.

This is the common concept about an anion-exchange membrane; based on this principle, the use of a salt solution is adopted as a conventional method in eluting adsorbed proteins.

In other words, the anion-exchange membrane is thought to adsorb no protein when a salt is present in the solution; this concept has been ditto for an anion-exchange membrane having graft chains.

In the porous membrane used in the present embodiment, anion-exchange groups are fixed to graft chains present on the surface of pores.

The present inventors have found the fact that the use of the porous membrane of the present embodiment, i.e. the anion-exchange membrane having anion-exchange groups fixed to graft chains, does not cause a significant reduction in the adsorption of a protein even in a solution containing a salt.

The adsorption of a protein is two-dimensional for a conventional porous membrane in which anion-exchange groups rest only on the surface of pores or a resin, whereas the fixation of anion-exchange groups to graft chains allows the anion-exchange groups to be three-dimensionally (sterically) placed. The fixation of anion-exchange groups to graft chains is thought to increase the number of anion-exchange groups responsible for adsorption because graft chains adsorb onto a protein in such a manner that the protein become entangled with the chains. The increased number of the anion-exchange groups involved in the adsorption causes little reduction in the adsorption of a protein even when a salt is present in the solution, which probably achieves the removal of dissolved impurities by adsorption even from a practical cell culture.

The porous membrane having anion-exchange groups used in the present embodiment refers to a porous membrane composed of a porous body having graft chains fixed to the surface of the porous body as a base material and its pores and anion-exchange groups chemically or physically fixed to the graft chains.

The base material for the porous membrane is not particularly limited; however, it is preferably composed of a polyolefin polymer for retention of mechanical properties.

Examples of the polyolefin polymer can include homopolymers of olefins such as ethylene, propylene, butylene and vinylidene fluoride, copolymers of two or more of the olefins, or copolymers of one or two or more of olefins and perhalogenated olefins.

Examples of the perhalogenated olefin can include tetrafluoroethylene and/or chlorotrifluoroethylene.

Among these base materials, preferred is polyethylene or polyvinylidene fluoride, more preferably polyethylene, in that they are raw materials excellent particularly in mechanical strength and providing a high adsorption volume.

Methods for introducing graft chains into the surface and pores of a porous membrane and further fixing anion-exchange groups to the graft chains include, for example, but not limited to, a method as disclosed in Japanese Patent Laid-Open No. 02-132132.

According to the present embodiment, the graft rate refers to the ratio (percentage) of the weight of the graft chains introduced into the base material before the fixation of anion-exchange groups to the graft chains, to the weight of the base material.

The graft rate is preferably from 10% to 250% (both inclusive), more preferably from 10% to 150% (both inclusive), still more preferably from 10% to 90% (both inclusive), yet more preferably from 30% to 60% (both inclusive).

The graft rate of 10% or more makes the adsorption volume of a protein significantly high and is practical.

The graft rate of 250% or less provides practical strength.

A salt solution is generally passed through the porous membrane in eluting the adsorbed protein, which is characterized by expanding the membrane volume; a higher graft rate results in a higher expansion coefficient. The expansion coefficient of the membrane volume due to the passage of the salt solution depends on the structures of the porous membrane and graft chain; however, it is about 2% or less for the graft rate of 60%, about 3% or less for 90%, and about 5% or less for 150%. A graft rate of 250% or less can make the expansion coefficient 10% or less; thus, a porous membrane having a graft rate of 250% or less is practically preferable.

According to the present embodiment, the graft chain introduced into the base material refers to a chain having a chemical structure which is not removed even by washing with an organic solvent such as dimethylformamide (DMF) after the introduction reaction.

Examples of the graft chain can include polymers of glycidyl methacrylate, vinyl acetate and hydroxypropyl acetate; however, preferred is a polymer of glycidyl methacrylate or vinyl acetate, more preferably a polymer of glycidyl methacrylate since anion-exchange groups are easily introduced thereinto.

The anion-exchange group is not particularly limited provided that it is an anion-exchange group capable of adsorbing an impurity protein, DNA, HCP, a virus, an endotoxin or the like dissolved in the mixture liquid; examples thereof can include a diethylamino (DEA, $Et_2N-$) group, a quaternary ammonium (Q, $R_3N^+-$) group, a quaternary aminoethyl (QAE, $R_3N^+-(CH_2)_2-$) group, a diethylaminoethyl (DEAE, $Et_2N-(CH_2)_2-$) group, and a diethylaminopropyl (DEAP, $Et_2N-(CH_2)_3-$) group. R is not particularly limited, and R's bonded to the same N may be the same or different; R preferably represents a hydrocarbon group such as an alkyl group, a phenyl group and an aralkyl group.

Examples of the quaternary ammonium group can include a trimethylamino group (a trimethylammonium group introduced into a graft chain, $Me_3N^+-$).

Preferred are DEA and Q, more preferably DEA since these groups are easily fixed chemically to the graft chain introduced into the porous membrane and provide a high adsorption volume.

The anion-exchange group can be fixed to the graft chain by ring-opening the epoxy group of the glycidyl methacrylate polymer forming the graft chain and adding an amine such as diethylamine and an ammonium salt such as diethylammonium or trimethylammonium.

Seventy percent or more, preferably 75% or more, more preferably 80% or more by mole fraction of the epoxy groups of the graft chain are preferably replaced with anion-exchange groups. The amount of the replacing anion-exchange groups being within the above range can make a porous membrane having a high dynamic adsorption volume.

The maximum pore size of the porous membrane is preferably from 0.1 μm to 0.8 μm (both inclusive), more preferably from 0.1 μm to 0.6 μm (both inclusive), still more preferably from 0.2 μm to 0.5 μm (both inclusive) to cut a turbid component and bacteria and yet to obtain a high flux.

According to the present embodiment, the maximum pore size of the porous membrane refers to a value as determined by a bubble point method as given in Examples.

The dynamic adsorption volume for proteins from a salt-free solution, which the porous membrane containing anion-exchange groups has is preferably 30 mg/mL or more, more preferably 50 mg/mL or more, still more preferably 70 mg/mL or more to effectively reduce loads on an affinity chromatography column in the purification step using affinity chromatography.

The dynamic adsorption volume when the buffer contains 0.1 mol/L of a salt is preferably 10 mg/mL or more, more preferably 20 mg/mL or more, still more preferably 30 mg/mL or more.

The amount of impurities adsorbed to an ion-exchange membrane is proportional to the volume of the ion-exchange membrane. Thus, the larger dynamic adsorption volume of the ion-exchange membrane can decrease the size of a module used for purifying a protein.

According to the present embodiment, the dynamic adsorption volume refers to the mass (in mg/mL) of a protein adsorbed by a porous membrane before breakthrough per volume of the porous membrane. Bovine serum albumin (BSA) is used as a model protein for estimating the adsorption volume; BSA dissolved in a 20 mM Tris-HCl (pH 8.0) buffer can be used to estimate the dynamic adsorption volume by a method as described in the following Examples.

The form of the porous membrane is not particularly limited provided that it is a porous body; examples thereof can include a flat membrane, nonwoven fabric, hollow fiber membrane, monolith, capillary, disk or cylinder form.

The porous membrane is preferably a hollow fiber membrane in view of ease of production, scalability, membrane packing properties in modular molding, and the like.

According to the present embodiment, the porous hollow fiber membrane having anion-exchange groups can be used in the harvest step before the downstream step employing affinity chromatography to filter an animal cell culture containing a target protein to provide a clear solution of the target protein. The porous hollow fiber membrane having anion-exchange groups can be used to remove impurity proteins, HCP, DNA, viruses and the like as non-turbid components, present in a dissolved state in the culture in addition to cells, cell debris and the like present as turbid components and yet remove bacteria to provide a clear target protein solution which is made free of impurities and sterilized.

For the purpose of obtaining a clear target protein solution from the cell culture, the porous hollow fiber membrane having anion-exchange groups is preferably housed in a module.

The porous hollow fiber membrane module is a module housing a porous hollow fiber membrane composed of a porous hollow fiber in which anion-exchange groups are chemically or physically fixed to the surface of the fiber and the surface of its pores. Using the porous hollow fiber membrane module, an animal cell culture can be passed therethrough to remove cells, cell debris and the like present as turbid components and dissolved impurity proteins, HCP, DNA, bacteria and the like present as non-turbid components from the culture. The cells, cell debris and the like present in the culture as turbid components can be removed by size filtering since they are large in size and thus cannot be passed through the pores of the porous hollow fiber. Impurity proteins and the like present dissolved in the culture can be removed by adsorption to the anion-exchange groups fixed to the surface of the porous hollow fiber and the surface of its pores.

According to the present embodiment, to remove impurities such as turbid and non-turbid components in an animal cell culture, a cross-flow filtration method is preferably used which involves passing a pressurized culture through the inside of a porous hollow fiber to pass the culture out to the outside of the porous hollow fiber.

The culture can be passed to the inside of the porous hollow fiber by cross-flow to inhibit the sedimentation of turbid material on the inside surface in passing the culture out to the outside of the porous hollow fiber to suppress a considerable reduction in the flux.

In the cross-flow filtration, the linear velocity of the liquid in flowing through the porous hollow fiber is preferably 0.05 m/s to 5.0 m/s, more preferably 0.1 m/s to 2.0 m/s.

According to the present embodiment, the linear velocity is the velocity of a liquid passing through the inner section of the porous hollow fiber, and is expressed by: (the volume of the liquid flowing through the porous hollow fiber per second)/(the inner sectional area of the porous hollow fiber).

The filtering liquid passage pressure from the inside of the porous hollow fiber to the outside thereof is preferably from 0.01 MPa to 0.5 MPa, more preferably from 0.05 MPa to 0.2 MPa.

According to the present embodiment, preferred methods for obtaining a clear solution of a target protein from an animal cell culture in a short time also include a method which involves subjecting the animal cell culture only to clarification treatment and then performing a filtration step using the porous hollow fiber membrane having anion-exchange groups. The animal cell culture can be subjected only to clarification treatment in advance before filtration using the porous hollow fiber membrane having anion-exchange groups to provide a high flux in the filtration step, enabling the filtration step employing the porous hollow fiber membrane to be performed by normal flow filtration.

The clarification treatment is preferably performed in advance because the filtration using the porous hollow fiber membrane having anion-exchange groups removes only non-turbid components such as residual cell debris, dissolved impurity proteins; HCP, DNA, and bacteria.

Non-limited examples of the clarification treatment of an animal cell culture can include a method using centrifugation, normal flow filtration with a depth filter such as a diatomaceous earth filter, or cross-flow filtration with a microfiltration membrane.

The liquid subjected to clarification treatment can be directly fed to filtration using the porous hollow fiber membrane having anion-exchange groups; thus, the cross-flow filtration with a microfiltration membrane is preferable, and cross-flow filtration with a microfiltration hollow fiber membrane module is more preferable.

The maximum pore size of the porous hollow fiber in the microfiltration hollow fiber membrane module used for clarification treatment is preferably from 0.1 μm to 0.8 μm, more preferably from 0.2 μm to 0.6 μm.

A smaller maximum pore size provides no sufficient flux, and a larger maximum pore size tends to cause plugging in subsequent normal flow filtration through the hollow fiber membrane module comprising the porous hollow fibers having anion-exchange groups according to the present embodiment, resulting in increased passage pressure.

In performing the clarification treatment by cross-flow filtration using the microfiltration hollow fiber membrane module, the linear velocity of the animal cell culture when flowing on the inner surface of the porous hollow fiber is preferably from 0.05 m/s to 5.0 m/s, more preferably from 0.1 m/s to 2.0 m/s.

The filtering liquid passage pressure from the inside of the porous hollow fiber to the outside thereof is preferably from 0.01 MPa to 0.5 MPa, more preferably from 0.05 MPa to 0.2 MPa.

Preferably, the method for purifying the protein according to the present embodiment further comprises the step of performing purification using affinity chromatography.

The purification using affinity chromatography can be carried out by a heretofore known method and can be performed using a protein A affinity column.

In this process, the clarified solution containing a target protein obtained by filtration using the porous membrane having anion-exchange groups is first applied to the protein A affinity column for the selective adsorption of the target protein.

The dissolved impurity proteins contained in the clarified solution are removed by outflow without adsorption to the protein A affinity column. Next, the column is washed with a buffer having the same pH as that of the clarified solution to remove impurities left in the column, and the adsorbed target protein can be then eluted and recovered using an acidic eluent to provide a solution of a purified target protein from which most of the impurity proteins have been further removed.

Even with impurity proteins being dissolved in a solution to be applied containing the target protein, the target protein can be purified using the protein A affinity column.

In the step of performing purification by affinity chromatography, a large amount of dissolved impurity proteins results in the presence of aggregated impurities in the recovered solution from the column, or reduces the life of the column because loads are applied to the column. Before application to the column, dissolved impurity proteins are preferably removed as much as possible in advance using the porous hollow fiber membrane having anion-exchange groups; thus, it is preferred to filter them using the porous membrane used in the present embodiment.

Examples of the affinity chromatography column used in the present embodiment can include columns having protein A, heparin, Con A, Red (Procion Red HE-3B), Blue (Cibacron Blue 3GA), lysine, arginine, benzamidine, and the like as ligands; when the target protein is an antibody, the protein A affinity chromatography column is often used.

The method for applying the clarified solution containing a target protein obtained by filtration using the porous membrane having anion-exchange groups to the affinity chromatography column for adsorption can be carried out by a method which involves, for example, supplying the clarified solution to the column after equilibrating using a pump or hydrostatic pressure.

The washing of the affinity chromatography column to which the target protein is adsorbed is not particularly limited provided that it uses a buffer having the same pH as that of the clarified solution containing the target protein; examples of the buffer can include a buffer such as a sodium-phosphate buffer.

The washing with the buffer can be carried out by passing a buffer having a volume of on the order of 2 to 10 times the column volume through the column.

The recovery of the target protein from the affinity chromatography column to which the target protein is adsorbed is not particularly limited provided that it uses a buffer of an acidic solution as an elution buffer; examples of the buffer can include acidic solutions such as a pH 3 to 4 citrate-NAOH buffer.

The recovery of the target protein using the acidic solution can be carried out by feeding the elution buffer at a volume of 2 to 10 times the column volume through the column.

The previously observed generation of aggregated impurities occurring in the recovery of a protein with an acidic solution can be suppressed by filtering an animal cell culture containing a target protein using the porous membrane having anion-exchange groups to provide a clear solution of the target protein and then purifying the clear solution of the target protein by affinity chromatography to recover the target protein. A mixture liquid containing a target protein can be filtered using the porous membrane employed in the present embodiment to reduce loads on the affinity column as well as to recover a highly purified target protein.

EXAMPLES

The present embodiment is more specifically described below based on Examples and Comparative Examples. However, the present embodiment is not intended to be limited only to these Examples. Estimation and measurement methods used in the present embodiment are as follows.

(1) Bubble Point Method

The bubble point method was used to measure the maximum pore size of a porous hollow fiber. One end of a porous hollow fiber 8 cm in length was blocked, and the other end was connected to a nitrogen gas supply line via a pressure indicator. Nitrogen gas was supplied in the connected state to replace the inside of the line with nitrogen, followed by immersing the porous hollow fiber in ethanol. At this time, the immersion was carried out in a state only slightly pressurized with nitrogen to avoid backflow of ethanol into the line. The pressure of nitrogen gas was slowly increased in a state in which the porous hollow fiber was immersed, and the pressure (p) at which bubbles of nitrogen gas started to stably occur from the porous hollow fiber was recorded.

The maximum pore size of the porous hollow fiber was calculated by $$d = C\gamma/p \quad (I)$$

wherein d is the maximum pore size and γ is the surface tension of the interface between ethanol and air.

Here, C is a constant. Because the immersion fluid is ethanol, C=0.632 (kg/cm); the maximum pore size d (μm) was determined by substituting p (kg/cm$^2$) into the above equation.

(2) Bacteria Challenge Test

A bacteria challenge test was carried out to determine the sterilization performance of minimodules as prepared in Examples 1, 2 and 6.

A 100 ppm sodium hypochlorite aqueous solution (200 mL) was fed to, and simultaneously passed through, the inside of the module in the manner of cross-flow for sterilization, and then extra pure water (500 mL) was similarly fed while passing therethrough for washing. Using *Pseudomonas dimunuta* as an indicator bacterium for a pore size of 0.22 μm, 200 mL of an aqueous solution containing a concentration of 10$^6$ cells/ML of the indicator bacteria was fed to, and simultaneously passed through, the inside thereof also in the manner of cross-flow. The amount of *Pseudomonas dimunuta* contained in the filtrate was measured, demonstrating that it was 10 cells/100 mL or less and the LRV (logarithmic reduction value) of the 0.22 μm indicator bacterium for the module was 7 or less. From this, it was determined that this module enabled almost complete sterilization.

(3) Preparation of Model Fluid for Animal Cell Culture Containing Target Protein A serum-free CHO cell culture containing no antibody protein was provided which had a salt concentration of about 0.9% by mass (0.15 M), a protein concentration of about 1 g/L and a cell density of 3.0×10$^7$/mL, and γ-globulin (from SIGMA) as a target protein was added thereto to a concentration of 1 g/L to prepare a model fluid for an animal cell culture containing the target protein and being not clarified.

In this model fluid, γ-globulin is a target protein, and all proteins derived from the cell culture containing a turbid component are impurity proteins.

(4) Analysis of Protein by SDS-PAGE

SDS-PAGE was used to analyze proteins in the culture having passed through each of the minimodules prepared in Examples 1, 2 and 6. The filtrate (10 μL) to be used for analysis was mixed with an equal amount of a sample treatment solution (Tris SDS sample treatment solution or Tris SDSβ ME sample treatment solution from Daiichi Pure Chemical Co., Ltd.), which was heat-treated at 100° C. for 5 minutes. The resultant sample was applied to a gel plate for electrophoresis (Multigel II. Mini from Daiichi Pure Chemical Co., Ltd.) in an amount of 10 μL per well using a micropipette, which was inserted into an electrophoresis tank (Easy-Separator™ from Wako Pure Chemical Industries Ltd.) filled with a phoresis buffer (SDS-Tris-glycin phoresis buffer from Daiichi Pure Chemical Co., Ltd. was used after 1/10 dilution). Phoresis was performed at a constant current of 30 mA for one hour to separate proteins in the filtrate. The gel plate after phoresis was stained using a staining reagent (InstantBlue from Funakoshi Corporation or 2D-Silver Staining Reagent-II from Daiichi Pure Chemical Co., Ltd.) to confirm protein bands.

(5) Quantification of HCP

The fluid to be estimated was applied to a 96-well plate in CHO Host Cell Protein ELISA Kit from Cygnus Technologies Inc. to quantify HCP as an impurity using Ultrospec Visible Plate Reader 1196 from GE Healthcare Bioscience Corporation as a plate reader.

(6) Quantification of DNA

The fluid to be estimated was treated using Quant-iT™ dsDNA HS Assay Kit from Invitrogen Corporation, followed by quantifying DNA as an impurity employing Qubit™ fluorometer.

(7) Adsorption Recovery of Target Protein by Protein A Affinity Column

Clear cultures obtained by passage through the minimodules prepared in Examples 1, 2 and 6 were each used as a sample fluid to estimate the adsorption recovery of a target protein therefrom by a protein A affinity column. The protein A affinity column (HiTrap Protein A HP 1 mL from GE Healthcare Bioscience Corporation) was connected to a commercially available chromatography system (AKTAexplorer100 from GE Healthcare Bioscience Corporation) for fluid-feeding. The buffer for equilibrating the column and washing after sample application used was 20 mM sodium-phosphate (pH 7.0), and the buffer for eluting the adsorbed target protein used was 0.1 M citric acid-NaOH (pH 3.0). In the adsorption estimation, the following five steps were carried out as one cycle to estimate the adsorption amount of a target protein: 1) pass 10 mL of the buffer for equilibration through the column; 2) pass a clear fluid containing the target protein through the column to adsorb the target protein thereto; 3) pass 10 mL of a buffer to the column to wash impurity proteins therein; 4) pass 10 mL of the elution buffer therethrough to elute and recover the adsorbed target protein; and 5) pass 10 mL of the buffer through the column to rewash it. At this time, the passage was performed at a flow rate of 1.0 mL/minute in each step. These cycles were continuously performed in the repeated estimation of the adsorption recovery of the target protein. The recovered solution was diluted by 1/10 and measured for ultraviolet absorbance at 280 nm to determine the amount of adsorption from the calibration curve obtained by ultraviolet absorbance measurements at known concentrations in advance.

(8) Microfiltration Hollow Fiber Membrane Module for Clarification

A minimodule for clarification was prepared by bundling 11 polysulfonate microfiltration hollow fibers having an outer diameter of 2.0 mm, an inner diameter of 1.4 mm and a maximum pore size of 0.4 μm and fixing both ends thereof to a polycarbonate-made module case using an epoxy potting agent so that the hollow parts of the hollow fibers were not blocked. The resultant minimodule had an inner diameter of 0.9 cm, a length of about 8 cm, and an effective membrane area of the hollow fiber inner surface in the module of 39 cm$^2$.

(9) Measurement of Dynamic Adsorption Volume

A BSA solution in which BSA was dissolved at a concentration of 1 g/L in a 20 mmol/L Tris-HCl (pH 8.0) buffer was used to pass the BSA solution through the estimation module until the start of its breakthrough. Here, from the concentration (Q) of a BSA solution, the volume ($V_B$) of the BSA solution passed through by the time the breakthrough of the estimation module occurred, and the volume ($V_B$) of an ion-exchange membrane according to each Example in the estimation module, the dynamic adsorption volume was calculated based on the equation (II) below:

$$A = Q \times V_B / V_M \tag{II}$$

The volume of an ion-exchange membrane is the volume of that from which the hollow portion thereof is subtracted. The breakthrough refers to a time point at which the concentration of BSA in the filtrate has exceeded 0.1 g/L, i.e. 10% of the concentration of the BSA solution supplied. The solution was passed from the inside of the hollow ion-exchange membrane toward the outside thereof in the estimation module. The dynamic adsorption volumes of the anion-exchange membranes prepared in Examples 1, 2 and 6 were 70 mg/mL, 35 mg/mL and 75 mg/mL, respectively, as measured by this method.

Example 1

(i) Introduction of Graft Chains into Porous Hollow Fiber Membrane

In an airtight container was placed porous polyethylene hollow fibers having an outer diameter of 3.0 mm, an inner diameter of 2.0 mm and a maximum pore size measured by the bubble point method described in the above (1) of 0.3 μm, and the air in the container was replaced with nitrogen. Then, the hollow fibers were irradiated with 200 of γ-ray to generate radical while cooling the container from the outside thereof with dry ice. The resultant radical-containing porous polyethylene hollow fibers were placed in a glass reaction tube, and the oxygen in the reaction tube was removed by depressurization to 200 Pa or less. A reaction solution containing 3 parts by volume of glycidyl methacrylate (GMA) and 97 parts by volume of methanol, adjusted at 40° C., was injected thereinto in an amount of 20 parts by mass to the hollow fibers and then allowed to stand in a closed state for 12 minutes to subject to graft polymerization reaction to introduce graft chains into the porous hollow fibers.

The mixed solution was bubbled with nitrogen in advance to replace the oxygen in the mixed solution with nitrogen.

After graft polymerization reaction, the reaction solution in the reaction tube was discarded. The hollow fibers were then washed by placing dimethylsulfoxide in the reaction tube to remove the residual glycidyl methacrylate, its oligomers and graft chains not fixed to the porous hollow fiber membranes.

After discarding the wash solution, washing was further carried out twice by placing dimethylsulfoxide therein. Using methanol, washing was similarly performed three times. When the hollow fibers after washing were dried and weighed, the weight of the porous hollow fiber membranes was 138% of that before introduction of graft chains and the graft rate defined as the ratio of the graft chain weight to the base material weight was 38%.

This is equivalent to the ratio of the number of moles of the introduced GMA (molecular weight: 142) to the number of moles of $CH_2$ groups (molecular weight: 14) as the skeleton unit of the base material polyethylene being 3.75% as calculated by the following equation (III).

$$\text{Mole Number \% of Introduced GMA} = (\text{Graft Rate}/142)/(100/14) \times 100 \tag{III}$$

The ratio of the number of moles of the polyethylene skeleton unit $CH_2$ group in the porous hollow fiber membrane after graft reaction and the number of moles of ester groups (COO groups) characteristic of GMA constituting the graft chain was measured by the solid NMR method.

Using 0.5 g of the powdered sample obtained by freezing and grinding the hollow fibers after graft reaction, the measurement was carried out at room temperature under conditions of a waiting time of 100 s and an integration of 1,000 times by the quantitative determination mode of the High Power Decoupling (HPDEC) method employing DSX400 from Bruker Biospin Corp. and the nuclide $^{13}C$.

The ratio of the peak area corresponding to the ester group and the peak area corresponding to the $CH_2$ group in the resultant NMR spectrum is equivalent to the ratio of the numbers of moles of GMA and $CH_2$ groups; thus, when the ratio of the number of moles of the introduced GMA to the number of moles of $CH_2$ groups was calculated from the measurement results, it was found to be 3.8%. This is equivalent to a graft rate of 38.5%; it was shown that the graft rate was obtained by measuring the sample after graft reaction by the solid NMR method.

(ii) Fixation of Anion-Exchange Group (Tertiary Amino Group) to Graft Chain

A dried hollow fiber into which graft chains were introduced was swollen by immersion in methanol for 10 minutes or more and then immersed in purified water for replacement with water. The hollow fiber after graft reaction (20 parts by mass) was placed in a glass reaction tube containing a reaction solution containing a mixed solution of 50 parts by volume of diethylamine and 50 parts by volume of purified water, and adjusted to 30° C. The porous hollow fiber into which graft chains were introduced was inserted thereinto and allowed to stand for 210 minutes to replace the epoxy groups of the graft chains with diethylamino groups to provide a porous hollow fiber membrane having diethylamino groups as anion-exchange groups.

The resultant porous hollow fiber membrane has an outer diameter of 3.3 mm and an inner diameter of 2.1 mm, and 80% of the epoxy groups of the graft chain in the porous hollow fiber membrane were replaced with diethylamino groups.

A replacement ratio T was calculated by the following equation (IV), assuming that T is the ratio of the number ($N_1$) of moles of epoxy groups replaced with diethylamino groups to the number ($N_2$) of moles of epoxy groups.

$$T = 100 \times N_1/N_2 = 100 \times \{(w_2-w_1)/M_1\}/\{w_1(dg/(dg+100))/M_2\} \tag{IV}$$

In this equation, $M_1$ is the molecular weight of diethylammonium (73.14); $w_1$ is the weight of the porous hollow fiber membrane after graft polymerization reaction; $w_2$ is the weight of the porous hollow fiber membrane after replacement reaction with the dimethylamino group; dg is the graft rate; and $M_2$ is the molecular weight of GMA (142).

In the same way as described above using the solid NMR method, the ratio of the number of moles of ester groups characteristic of GMA to the number of moles of $CH_2$ groups as polyethylene skeleton units in the porous hollow fiber membrane into which diethylamino groups were introduced was measured. As a result, it was found to be 3.75%. This was equivalent to the graft rate of 38%. From this result, it was determined that there was no change in the graft rate due to the introduction of diethylamino groups.

(iii) Preparation of Anion-Exchange Membrane Module

A hollow fiber module for the anion-exchange membrane was prepared by bundling three porous hollow fibers having diethylamino groups as anion-exchange groups and fixing both ends thereof to a polysulfonate-made module case using an epoxy potting agent so that the hollow parts of the porous hollow fibers were not blocked.

The resultant module had an inner diameter of 0.9 cm, a length of about 3.3 cm, a module inner volume of about 2 mL, an effective volume of the porous hollow fibers in the module of 0.85 mL, and a volume of only porous hollow fiber membranes from which hollow parts were subtracted of 0.54 mL.

Example 2

(iv) Fixation of Anion-Exchange Groups (Quaternary Amino Groups) to Graft Chain

In the same way as in Example 1, a dried hollow fiber into which graft chains were introduced was swollen by immersion in methanol for 10 minutes or more, and then immersed in purified water for replacement with water. A mixed solution containing 50 parts by volume of purified water and 50 parts by volume of dimethylsulfoxide was provided, and trimethylammonium chloride was added to a concentration of 0.5M to the mixed solution, which was then mixed to provide a uniform reaction solution. The reaction solution was placed in a glass reaction tube in an amount of 20 parts by mass to the hollow fiber after graft reaction, and adjusted to 60° C. The porous hollow fiber into which graft chains were introduced was then inserted thereinto and allowed to stand for 200 minutes to replace the epoxy groups of the graft chains with trimethylamino groups to provide a porous hollow fiber membrane having trimethylamino groups as anion-exchange groups.

The resultant porous hollow fiber membrane had an outer diameter of 3.2 mm and an inner diameter of 2.1 mm, and 80% of the epoxy groups of the graft chain were replaced with trimethylamino groups. The replacement ratio was calculated in the same way as for the diethylamino group by substituting the molecular weight of trimethylammonium chloride (95.57) into $M_1$ in the above equation (IV).

(v) Preparation of Anion-Exchange Membrane Module

A porous hollow fiber membrane module having trimethylamino groups as anion-exchange groups was also prepared in the same way as in Example 1. A module was obtained which has an effective volume of the porous hollow fibers of 0.75 mL and a volume of only porous hollow fiber membranes from which hollow parts were subtracted of 0.46 mL.

Example 3

NaCl was added to 20 mM Tris-HCl (pH 8.0) to a concentration of 0.17 M to prepare a metal salt-containing buffer. In this buffer dissolved were BSA (pI: 5.6) and γ-globulin at a concentration of 1 g/L each to prepare a mixed solution of proteins. This mixed solution of proteins was passed through the anion-exchange membrane module having diethylamino groups prepared in Example 1 at a flow rate of 2 mL/minute, and the filtrate was collected in the form of 5 mL each of fractions. SDS-PAGE was used to analyze proteins in the fractions having passed through the module. The filtrate (10 µL) to be used for the analysis was mixed with an equal amount of a sample treatment solution (Tris SDS sample treatment solution from Daiichi Pure Chemical Co., Ltd.), which was then heat-treated at 100° C. for 5 minutes. The resultant sample was applied to a gel plate for electrophoresis (Multigel II Mini from Daiichi Pure Chemical Co., Ltd.) in an amount of 10 µL per well using a micropipette, which was inserted into an electrophoresis tank (EasySeparator™ from Wako Pure Chemical Industries Ltd.) filled with a phoresis buffer (SDS-Tris-glycin phoresis buffer from Daiichi Pure Chemical Co., Ltd. was used after 1/10 dilution) to perform phoresis at a constant current of 30 mA for one hour to separate the proteins in the filtrate. The gel plate after phoresis was stained using a staining reagent (InstantBlue from Funakoshi Corporation).

Figure 1:
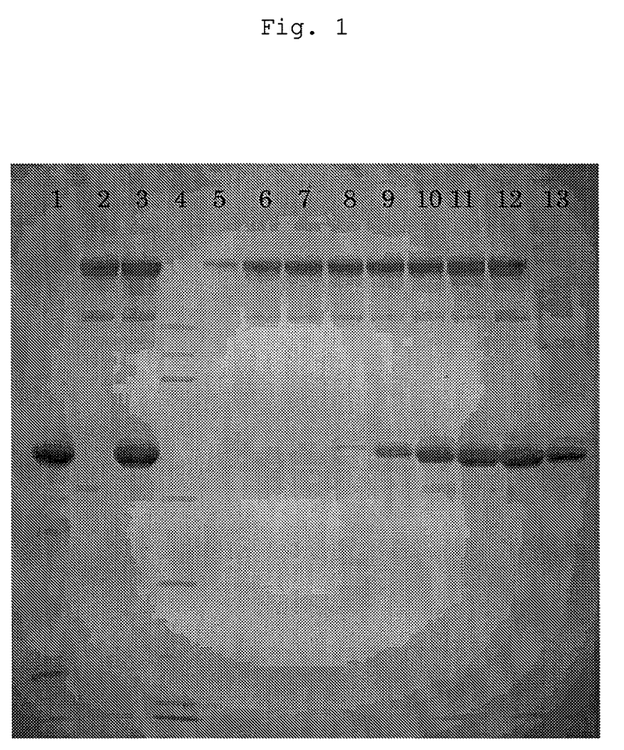
FIG. 1 shows results of the SDS-PAGE analysis of straightly passed-through and adsorbed components in the filtration of a mixture liquid of BSA and γ-globulin using an anion-exchange hollow fiber membrane module in Example 3.

The results obtained are shown in FIG. 1. Lane 1 is. BSA; lane 2 is γ-globulin alone; lane 3 is a mixture liquid of BSA and γ-globulin; lanes 5 to 12 are fractions of the filtrate; and lane 13 is an eluate of adsorbate. There was the almost exclusive presence of γ-globulin in the filtrate reaching up to 20 mL (lanes 5 to 8); BSA was totally adsorbed. After adsorption, elution was carried out using a salt solution in which 1 M NaCl was dissolved in a buffer. There was the exclusive presence of BSA in the eluate (lane 13): only BSA was selectively adsorbed to the module and γ-globulin was non-adsorbed. The results shown in FIG. 1 indicated that the method of the present embodiment is effective for separating a target protein from a salt-containing solution.

Example 4

A serum-free CHO cell culture containing 0.5 g/L of γ-globulin as a target protein was subjected to dead end filtration using a microfiltration hollow fiber membrane module to provide a clarified supernatant. This supernatant fluid (54 mL (equivalent to 100 times the hollow fiber membrane volume)) was passed at a flow rate of 2 mL/minute through the anion-exchange membrane module having diethylamino groups prepared in Example 1 to collect all the filtrate. SDS-PAGE was used to estimate proteins in the fractions having passed through the module. The filtrate (10 µL) to be used for the analysis was mixed with an equal amount of a sample treatment solution (Tris SDSβ ME sample treatment solution from Daiichi Pure Chemical Co., Ltd.), which was then heat-treated under reduction at 100° C. for 5 minutes. The resultant sample was applied to a gel plate for electrophoresis (Multigel II Mini from Daiichi Pure Chemical Co., Ltd.) in an amount of 10 µL per well using a micropipette, which was inserted into an electrophoresis tank (EasySeparator™ from Wako Pure Chemical Industries Ltd.) filled with a phoresis buffer (SDS-Tris-glycin phoresis buffer from Daiichi Pure Chemical Co., Ltd. was used after 1/10 dilution). Phoresis was performed at a constant current of 30 mA for one hour to separate proteins in the filtrate.

The gel plate after phoresis was stained using a staining reagent (2D-Silver Staining Reagent-II from Daiichi Pure Chemical Co., Ltd.).

Figure 2:
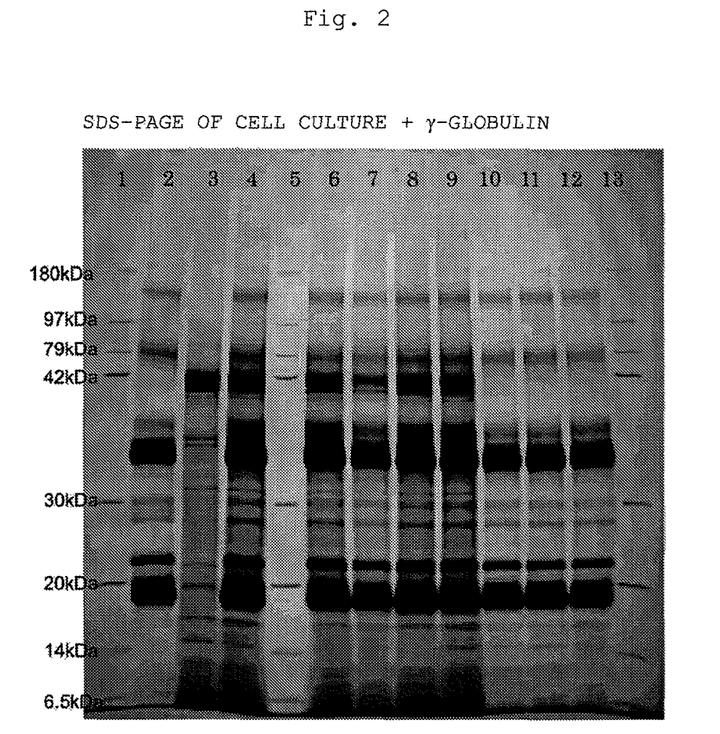
FIG. 2 shows results of the SDS-PAGE analysis of the purification of a γ-globulin-containing cell culture by filtration using various anion-exchange membranes in Examples 4 to 6 and Comparative Example 1.

The results obtained are shown in FIG. 2. Lane 2 is γ-globulin alone; lane 3 is a serum-free CHO cell culture supernatant alone; lanes 4 and 9 are serum-free CHO cell culture supernatants containing γ-globulin; and lane 10 is the filtrate for this estimation. It was shown that passage through the anion-exchange membrane module removed much impurities in the salt-containing cell culture to provide a purified target protein. The concentrations of HCP and DNA as typical impurities were 346 µg/mL and 7,200 ng/mL, respectively in the cell culture supernatant before passage through the anion-exchange membrane module and considerably decreased to 39 µg/mL and 52 ng/mL, respectively in the filtrate, indicating that this method was excellent in the property of removing these protein impurities present in a dissolved state.

Example 5

Using the anion-exchange membrane module containing trimethylamino groups prepared in Example 2, in the same way as in Example 4, the same supernatant of the serum-free CHO cell culture containing 0.5 g/L of γ-globulin as a target protein was passed therethrough in an amount of 46 mL equivalent to 100 times the membrane volume to remove impurities. Estimation using SDS-PAGE was performed in the same way as in Example 4. The results are shown as in Example 4 in FIG. 2. Lane 12 is the filtrate for this estimation. It was shown that passage through the anion-exchange membrane module removed much impurities in the salt-containing cell culture to provide a purified target protein. The concentrations of HCP and DNA as typical impurities were 346 μg/mL and 7,200 ng/mL, respectively in the cell culture supernatant before passage through the anion-exchange membrane module and considerably decreased to 73.8 μg/mL and 32.8 ng/mL, respectively in the filtrate, indicating that this method was excellent in the property of removing these protein impurities present in a dissolved state.

Example 6

The introduction of graft chains and the fixation of diethylamino groups to the graft chains were carried out in the same way as in Example 1 except for the composition of the reaction solution containing 10 parts by volume of glycidyl methacrylate and 90 parts by volume of methanol to provide a porous hollow fiber membrane containing diethylamino groups as anion-exchange groups and having a graft rate of 140%. As the result of calculation using the equation (IV), 93% of the epoxy groups of the graft chain were replaced by diethylamino groups. The resultant porous hollow fiber membrane had an outer diameter of 4.0 mm and an inner diameter of 2.5 mm. This porous hollow fiber membrane was used to prepare a hollow fiber module having an effective volume of the porous hollow fibers of 1.53 mL and a volume of only porous hollow fiber membranes from which hollow parts were subtracted of 0.92 mL in the same way as in Example 1.

Lane 11 in FIG. 2 shows the result of the estimation performed in the same way as in Example 4 using the hollow fiber module. It was shown that passage through the module removed many impurities in the salt-containing cell culture to provide a purified target protein. The concentrations of HCP and DNA as typical impurities were 346 μg/mL and 7,200 ng/mL, respectively in the cell culture supernatant before passage through the anion-exchange membrane module and considerably decreased to 42.6 μg/mL and 32.8 ng/mL, respectively in the filtrate, indicating that this method is excellent in the property of removing these impurities present in a dissolved state.

Comparative Example 1

Using 3 types of commercially available membranes having anion-exchange groups, i.e. SartobindQ MA75 (membrane volume: 2.06 mL) from Sartorius AG, MustangQ Acrodisc (membrane volume: 0.18 mL) from Pall Corporation, and BioCap 25 Filter 90ZA (membrane volume: 5 mL or more) from Cuno Incorporated, a supernatant of a serum-free CHO cell culture containing 0.5 g/L of γ-globulin as a target protein was passed therethrough in volumes equivalent to 100 times the respective membrane volumes in the same way as in Example 4 to remove impurities. Estimation using SDS-PAGE was performed in the same way as in Example 4. The results are shown as in Example 4 in FIG. 2. Lane 6 was a filtrate of SartobindQ MA75; lane 7 was a filtrate of MustangQ Acrodisc; and lane 8 was a filtrate of BioCap 25 Filter 90ZA. These results showed that the use of the commercially available membranes having anion-exchange groups did not allow the effective removal of impurities from the salt-containing cell culture. The concentrations of HCP and DNA in the cell culture supernatant before passage through the anion-exchange membrane module were 346 μg/mL and 7,200 ng/mL, respectively, whereas those after the passage were 269 μg/mL and 492 ng/mL, respectively, for SartobindQ MA75, 248 μg/mL and 3,916 ng/mL, respectively, for MustangQ Acrodisc, and 310 μg/mL and 7,600 ng/mL, respectively, for BioCap 25 Filter 90ZA. These results indicated that this method was inferior in the property of removing impurities to the method of the present embodiment.

Example 7

Protein A Purification of Solution Having Passed Through DEA Anion-Exchange Membrane The solution having passed through a hollow fiber membrane module having diethylamino groups obtained in Example 4 was used as a cell culture from which dissolved impurities were removed to purify γ-globulin therefrom by adsorption and recovery using a protein A affinity column. According to the method described in the above (7), 30 mL of the filtrate of Example 4 was passed through the protein A affinity column to adsorb γ-globulin, followed by purification and recovery using an elution buffer. The recovered solution was diluted by 1/10 and measured for ultraviolet absorption intensity to estimate the recovery amount. As a result, 14.2 mg of γ-globulin was contained in the recovered solution; the recovery rate was found to be 95%. The concentrations of HCP and DNA contained in the recovered solution were 0.162 μg/mL and 11.8 ng/mL, respectively; thus, the method of the present embodiment was shown to have a high recovery rate and be excellent in the property of removing impurities.

Example 8

Protein A Purification of Solution Having Passed Through TMA Anion-Exchange Membrane The solution having passed through a hollow fiber membrane module having trimethylamino groups obtained in Example 5 was used as a cell culture from which dissolved impurities were removed to purify γ-globulin therefrom by adsorption and recovery using a protein A affinity column as described in Example 7. According to the method described in the above (7), 30 mL of the filtrate of Example 5 was passed through the protein A affinity column to adsorb γ-globulin, followed by purification and recovery using an elution buffer. The recovered solution was diluted by 1/10 and measured for ultraviolet absorption intensity to estimate the recovery amount. As a result, 13.8 mg of γ-globulin was contained in the recovered solution; the recovery rate was found to be 92%. The concentrations of HCP and DNA contained in the recovered solution were 0.289 μg/mL and 19.1 ng/mL, respectively; thus, the method of the present embodiment was shown to have a high recovery rate and be excellent in the property of removing impurities.

Example 9

Protein A Purification of Solution Having Passed Through DEA Anion-Exchange Membrane (2)

The solution having passed through a hollow fiber membrane module having diethylamino groups obtained in Example 6 was used as a cell culture from which dissolved impurities were removed to purify γ-globulin therefrom by adsorption and recovery using a protein A affinity column. According to the method described in the above (7), 30 mL of the filtrate of Example 6 was passed through the protein A affinity column to adsorb γ-globulin, followed by purification and recovery using an elution buffer. The recovered solution was diluted by ¹⁄₁₀ and measured for ultraviolet absorption intensity to estimate the recovery amount. As a result, 13.9 mg of γ-globulin was contained in the recovered solution; the recovery rate was found to be 93%. The concentrations of HCP and DNA contained in the recovered solution were protein A affinity column were diluted by ¹⁄₁₀ and measured for ultraviolet absorption intensity to estimate the rate of recovery from the solutions having passed through the respective anion-exchange membranes. As a result, the recovery rate was high for each of the membranes, i.e. 97% for SartobindQ MA75, 93% for MustangQ Acrodisc, and 95% for BioCap 25 Filter 90ZA. The concentrations of HCP and DNA in the recovered solutions were 3.83 μg/mL and 32.6 ng/mL, respectively for SartobindQ MA, 2.54 μg/mL and 46 ng/mL, respectively for MustangQ Acrodisc, and 3.27 μg/mL and 88.2 ng/mL, respectively for BioCap 25 Filter 90ZA. Thus, this method was inferior in the property of removing impurities to the method of the present embodiment and only provided almost the same purification degree as for Comparative Example 2 in which no passage treatment using an anion-exchange membrane was carried out.

The concentrations of HCP and DNA obtained in Examples 4 to 9 and Comparative Examples 1 to 3 were shown in Table 1. The results of Table 1 showed that the excellent property of removing impurities was obtained in each of Examples 4 to 9.

TABLE 1

|  | Treatment method | Filtrate | | Solution recovered from protein A column | |
|---|---|---|---|---|---|
|  |  | HCP (μg/mL) | DNA (ng/mL) | HCP (μg/mL) | DNA (ng/mL) |
| Examples 4 and 7 | Diethylamino group module | 39 | 52 | 0.162 | 11.8 |
| Examples 5 and 8 | Trimethylamino group module | 73.8 | 32.8 | 0.289 | 19.1 |
| Examples 6 and 9 | Diethylamino group module | 42.6 | 32.8 | 0.186 | 13.8 |
| Comparative Example 2 | Untreated | 346 | 7200 | 2.93 | 63.2 |
| Comparative Examples 1 and 3 | SartobindQ | 269 | 492 | 3.83 | 32.6 |
|  | MustangQ | 248 | 3916 | 2.54 | 46 |
|  | BioCap 90ZA | 310 | 7600 | 3.27 | 88.2 |

0.186 μg/mL and 13.8 ng/mL, respectively; thus, the method of the present embodiment was shown to have a high recovery rate and be excellent in the property of removing impurities.

Comparative Example 2

Purification was estimated as described in Example 7, using the cell culture containing 0.5 mg/mL of γ-globulin, subjected only to clarification with a microfiltration membrane, obtained in Example 4 as a cell culture from which dissolved impurities were not removed. The solution recovered from the protein A affinity column was diluted by ¹⁄₁₀ and measured for ultraviolet absorption intensity to estimate the recovery amount. As a result, 14.5 mg of γ-globulin was contained in the recovered solution; the recovery rate was found to be 97%. The concentrations of HCP and DNA contained in the recovered solution were 2.93 μg/mL and 63.2 ng/mL, respectively. The rate of recovery of the target protein was high, but much impurities were contained in the recovered solution in comparison to the case where the impurity removal was not performed using the hollow fiber membrane module having anion-exchange groups according to the present embodiment.

Comparative Example 3

The solutions having passed through commercially available anion-exchange membranes obtained in Comparative Example 1 were used to purify γ-globulin therefrom by adsorption and recovery using a protein A affinity column as described in Example 7. The solutions recovered from the

Example 10

Figure 3:
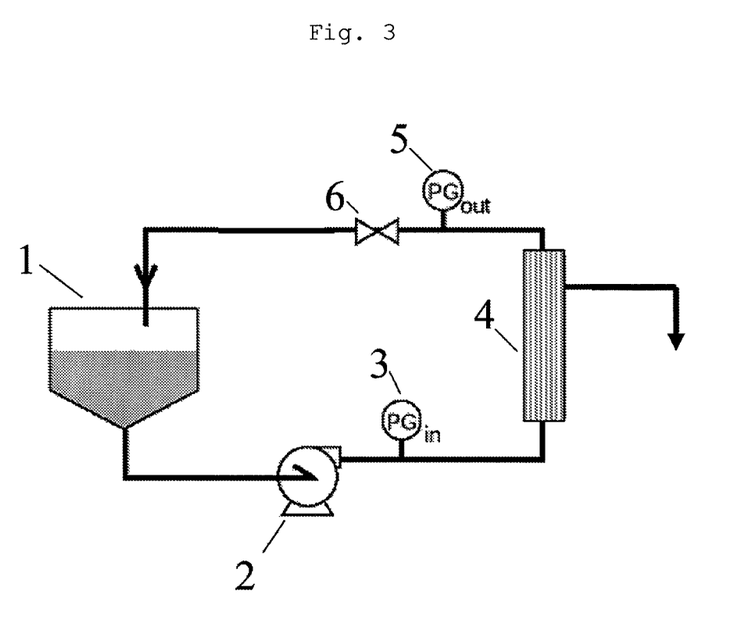
FIG. 3 illustrates a schematic drawing of an estimation apparatus for performing clarification, impurity protein removal and sterilization by a single step using an anion-exchange hollow fiber membrane module in Example 10.

The cross-flow filtration estimation apparatus shown in FIG. 3 was set up; 300 mL of the cell culture containing a target protein prepared in the above (3) was placed in a cell culture tank 1 and, using a perister pump 2, the culture was passed at a linear velocity of 0.5 m/s through a hollow fiber membrane module comprising porous hollow fiber membranes having diethylamino groups as anion-exchange groups as prepared in Example 1 (hereinafter referred to as an anion-exchange hollow fiber module) 4 for cross-flow filtration. Here, internal pressure type filtration was adopted by which the filtrate moved from the inside of the porous hollow fiber toward the outside thereof. The passage pressure was regulated by a flow control cock 6 so that the average of the pressures measured with a pressure indicator 3 (at the entry side of the module) and a pressure indicator 5 (at the exit side of the module) was 0.1 MPa, and 30 mL each of the solutions having passed through the module were collected so as to provide a total amount of 210 mL, followed by final collection of 40 mL of the solution and thereby the cross-flow filtration was performed until the total amount of the filtrate reached 250 mL. During the filtration, the average flux was 21 L/m²/hr (21 LMH). All of the filtrates collected were found to be clear by visual observation.

Figure 4:
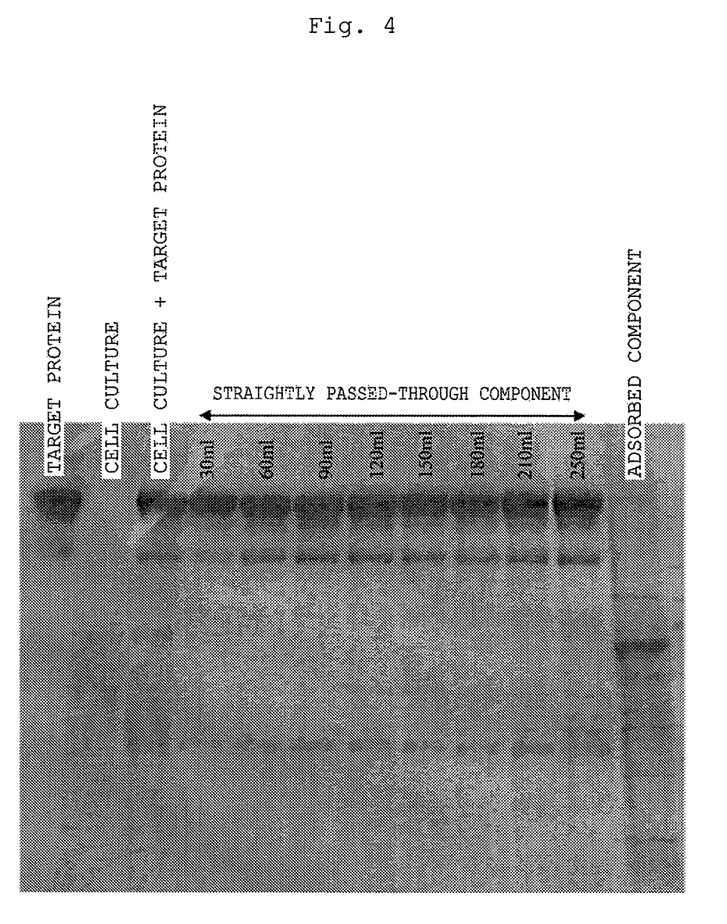
FIG. 4 shows results of the SDS-PAGE analysis of straightly passed-through and adsorbed components in the filtration using an anion-exchange hollow fiber membrane module in Example 10.

FIG. 4 shows the results of the SDS-PAGE of the filtrates and eluates performed according to the method described in the above (4). For all of the filtrates collected, the target protein straightly passed therethrough into the filtrate at the same concentration as that of the stock solution, and it was also shown that impurity proteins were evidently adsorbed by the anion-exchange hollow fiber membrane module. The anion-exchange hollow fiber membrane module after cross-flow filtration estimation was back washed with the buffer of 20 mM Tris-HCl (pH 8.0) to remove a turbid component deposited inside the porous hollow fiber, followed by eluting the adsorbed components using a buffer solution containing 1 M NaCl to analyze the eluate by SDS-PAGE. It was shown that a large amount of impurity proteins were adsorbed to the anion-exchange hollow fiber membrane module, while the target protein was not adsorbed to the module.

All of the clear cultures obtained by the passage placed in the same container to make a uniform solution, which was then passed through an unused protein A affinity column to estimate the amount of the target protein adsorbed to the protein A affinity column according to the method described in the above (7). Here, the amount of the culture passed through the column was 10 mL. In the estimation, the cycle of adsorption estimation described in the above (7) was repeated 10 times to measure the change of the adsorption amount. As a result, the adsorption amount in the first cycle was 9.8 mg and the adsorption amount in the tenth cycle was 9.8 mg, showing no decrease in the adsorption amount during the 10 times repetition. When the eluates were visually observed, the eluates were found to be clear in all of the estimations and no aggregates were identified. After the end of estimation, when the protein A affinity column was disassembled to observe inside beads under an optical microscope, no adhesion of impurities to the beads was seen. From these results, it was determined that the clarification of a cell culture and the removal of dissolved impurity proteins can be simultaneously carried out using the anion-exchange hollow fiber membrane module, which can greatly reduce loads on a protein A affinity column.

Comparative Example 4

Porous polyethylene hollow fibers comprising no anion-exchange groups, having an inner diameter of 3.0 mm and an outer diameter of 2.0 mm were used to prepare a minimodule by the same method as for the anion-exchange hollow fiber membrane module described in Example 1. Using this minimodule, a filtrate of a cell culture containing a target protein was collected in the same way as in Example 3. The resultant filtrate was clear by visual observation; however, when it was analyzed by SDS-PAGE according to the method described in the above (4), it was determined that an extremely large amount of impurity proteins were dissolved therein compared to the filtrate of Example 10. In addition, when the minimodule after estimation was back washed with a buffer as described in Example 10 and then eluted with a 1 M NaCl buffer solution, no impurity protein or target protein was shown to be adsorbed to the minimodule.

The clear culture obtained by the passage was passed through an unused protein A affinity column as described in Example 10 to estimate the adsorption amount of the target protein. When the estimation was repeated 10 times without exchanging the column to measure the change of the adsorption amount, the adsorption amount in the first estimation was 9.8 mg; however, the adsorption amount decreased with increasing number of repeats, resulting in the adsorption amount in the tenth estimation being 9.4 mg. When the eluate was visually observed, white turbidity, although slight, due to aggregates was identified. After the end of estimation, when the protein A affinity column was disassembled to observe inside beads under an optical microscope, adhesion of aggregated impurities to the beads was seen. This showed that the removal of dissolved impurity proteins was important for the reduction of loads on the protein A affinity column, demonstrating the effect of the porous hollow fiber membrane having anion-exchange groups.

Example 11

Figure 5:
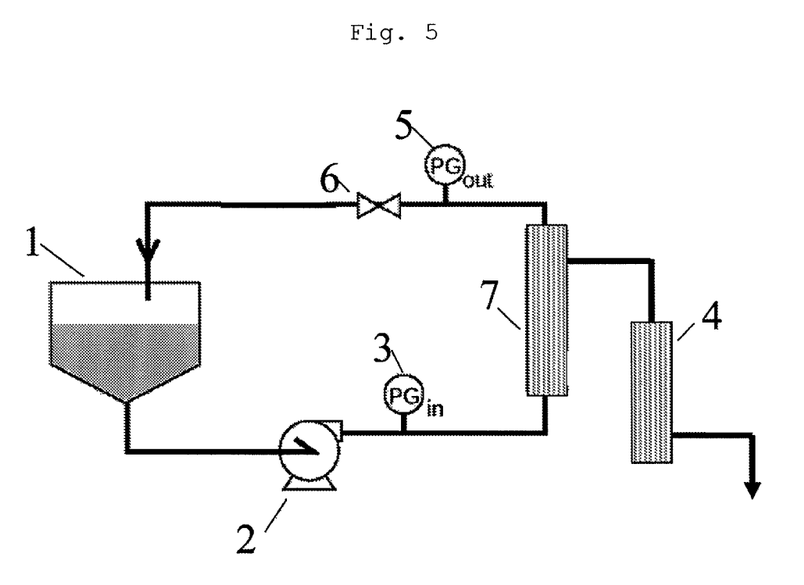
FIG. 5 illustrates a schematic drawing of an estimation apparatus for performing impurity protein removal and sterilization by 2 steps using an anion-exchange hollow fiber membrane module after clarification with a microfiltration hollow fiber membrane module in Example 11.

The cross-flow filtration estimation apparatus shown in FIG. 5 was set up; 300 mL of the cell culture containing a target protein prepared in the above (3) was placed in a cell culture tank 1 and, using a perister pump 2, the culture was passed in cross-flow at a linear velocity of 0.5 m/s through the microfiltration hollow fiber membrane module 7 for clarification described in the above (8) for filtration. The passage pressure was regulated by a flow control cock 6 so that the average of the pressures measured with a pressure indicator 3 (at the entry side of the module) and a pressure indicator 5 (at the exit side of the module) was 0.1 MPa. The solution having passed through the microfiltration hollow fiber membrane module 7 for clarification was directly fed to the same anion-exchange hollow fiber membrane module 4 as that of Example 10 to collect 30 mL each of the filtrates obtained by normal flow filtration. The time taken until the total filtrate amount reached 250 mL was 160 minutes, and the average flux was 120 L/m$^2$/hr (120 LMH). All of the filtrates collected were found to be clear by visual observation.

When the filtrates collected according to the method described in the above (4) were analyzed using SDS-PAGE, for all of the filtrates collected, the target protein had straightly passed therethrough into the filtrate at the same concentration as that of the stock solution, and it was also shown that impurity proteins had been evidently adsorbed by the anion-exchange hollow fiber membrane module.

Example 12

Using the microfiltration hollow fiber membrane module described in the above (8), the animal cell culture containing a target protein prepared in the above (3) was filtered to provide 300 mL of a clarified (clear) solution. After completely blocking the flow control cock 6 in the estimation apparatus of FIG. 3, the resultant clear solution was placed in the cell culture tank 1 of FIG. 3 and, using the perister pump 2, fed at a feed flow rate of 10 mL/minute therefrom to the same anion-exchange hollow fiber membrane module 4 as that of Example 10 to collect 30 mL each of the filtrates obtained by normal flow filtration. The time taken until the total filtrate amount reached 250 mL was 25 minutes, and the average flux was 816 L/m$^2$/hr (816 LMH). All of the filtrates collected were found to be clear by visual observation. From these results, it was determined that even the culture containing dissolved impurity proteins could be subjected to microfiltration before performing the filtration thereof using the anion-exchange hollow fiber membrane module to remove the impurity proteins at an extremely high processing speed.

When the filtrates collected according to the method described in the above (4) were analyzed by SDS-PAGE, for all of the filtrates collected, the target protein had straightly passed therethrough into the filtrate at the same concentration as that of the stock solution, and it was also shown that impurity proteins had been evidently adsorbed by the anion-exchange hollow fiber membrane module.

As described above, dissolved impurity proteins were capable of being markedly removed in Examples 3 to 12 in which filtration was performed using the anion-exchange hollow fiber membrane modules comprising porous hollow fiber membranes having anion-exchange groups prepared in Examples 1, 2 and 6 compared to in Comparative Examples 1, 3 and 4 in which the polyethylene hollow fiber membrane modules given no anion-exchange groups were used, or to in Comparative Example 2 in which no anion-exchange hollow fiber membrane module was used; the solutions of the target protein having a higher purity were also capable of being obtained when purification was performed using affinity chromatography. Particularly in Example 10, even when the solution obtained by performing the filtration was repeatedly applied to the protein A affinity column, the purifying capability of the column was not reduced, the adhesion of impurities to the column was prevented, and loads on the column were sufficiently diminished.

In addition, filtration was performed using the microfiltration hollow fiber membrane module before filtration with the anion-exchange hollow fiber membrane module to enable the filtration step employing the anion-exchange hollow fiber module to be performed at an extremely high processing speed. Filtration using the anion-exchange hollow fiber module could also be performed by normal flow filtration to markedly remove dissolved impurity proteins.

The present application is based on Japanese Patent Application No. 2007-279406 filed Oct. 26, 2007, the content of which is incorporated herein by reference.

INDUSTRIAL APPLICABILITY

The use of the method for purifying the protein according to the present embodiment enables the clarification of a cell culture before an affinity chromatography step, conventionally carried out by the three steps of centrifugation, microfiltration and sterilization filtration to be completed by the single step of filtration using a porous hollow fiber membrane having anion-exchange groups. As a result, reduction in cost is made possible by simplifying the process and contracting necessary equipment. Loads in the step of affinity chromatography can also be considerably reduced to more highly purify a desired protein as well as to achieve reduced cost of the purification.

The invention claimed is:

1. A method for purifying a protein to remove impurities from a mixture liquid containing a desired protein and the impurities, comprising:
performing filtration using a porous hollow fiber membrane having a graft chain on a pore surface and an anion-exchange group fixed to the graft chain, wherein:
a base material of the porous hollow fiber membrane is polyethylene or polyvinylidene fluoride,
the graft chain is polymers of glycidyl methacrylate and has a graft rate of from 10% to 90% (both inclusive), and
the graft chain has 70% or more of epoxy groups replaced with the anion-exchange group.

2. The method for purifying the protein according to claim 1, wherein the desired protein is one selected from the group consisting of monoclonal antibodies, polyclonal antibodies, humanized antibodies, human antibodies and immunoglobulins.

3. The method for purifying the protein according to claim 1, wherein the impurities are at least one selected from the group consisting of a non-turbid component and a turbid component dispersed in the mixture liquid.

4. The method for purifying the protein according to claim 3, wherein the non-turbid component is at least one selected from the group consisting of impurity proteins, HCP, DNA, viruses, endotoxins, proteases and bacteria dissolved in the mixture liquid.

5. The method for purifying the protein according to claim 3, wherein the turbid component dispersed in the mixture liquid is at least one selected from the group consisting of cells and cell debris.

6. The method for purifying the protein according to claim 1, wherein a salt concentration of the mixture liquid is from 0.01 M to 0.5 M (both inclusive).

7. The method for purifying the protein according to claim 1, wherein a salt concentration of the mixture liquid is from 0.1 M to 0.3 M (both inclusive).

8. The method for purifying the protein according to claim 1, wherein the graft rate is from 30% to 60% (both inclusive).

9. The method for purifying the protein according to claim 1, wherein the anion-exchange group is a diethylamino group and/or a trimethylamino group.

10. The method for purifying the protein according to claim 1, wherein the anion-exchange group is a diethylamino group.

11. The method for purifying the protein according to claim 1, wherein the porous membrane has a maximum pore size of from 0.1 μm to 0.8 μm (both inclusive).

12. The method for purifying the protein according to claim 1, wherein the mixture liquid is filtered using the porous membrane to remove one or more impurities comprising a non-turbid component.

13. The method for purifying the protein according to claim 1, wherein the mixture liquid is an animal cell culture.

14. The method for purifying the protein according to claim 1, wherein the porous membrane is a porous hollow fiber membrane.

15. The method for purifying a protein according to claim 1, further comprising performing purification using affinity chromatography.

16. A porous hollow fiber membrane having a graft chain on a pore surface and an anion-exchange group fixed to the graft chain, wherein:
a base material of the porous hollow fiber membrane is polyethylene or polyvinylidene fluoride,
the graft chain is polymers of glycidyl methacrylate and has a graft rate of from 10% to 90% (both inclusive), and
the graft chain has 70% or more of epoxy groups replaced with the anion-exchange group.

17. The porous hollow fiber membrane according to claim 16, wherein the graft rate is from 30% to 60% (both inclusive).

18. The porous hollow fiber membrane according to claim 16, wherein the porous membrane has a maximum pore size of from 0.1 μm to 0.8 μm (both inclusive).

19. A module comprising the porous hollow fiber membrane according to claim 16.

* * * * *